United States Patent [19]

Nelson

[11] Patent Number: 4,833,730
[45] Date of Patent: May 30, 1989

[54] BACK BRACE

[76] Inventor: Ronald E. Nelson, 405 Sunset La., Cambridge, Minn. 55008

[21] Appl. No.: 122,468

[22] Filed: Nov. 19, 1987

[51] Int. Cl.⁴ .................................................. A61F 5/02
[52] U.S. Cl. ........................................... 2/44; 450/144
[58] Field of Search ................................ 2/44; 450/144

[56] References Cited

U.S. PATENT DOCUMENTS

| | | | |
|---|---|---|---|
| 605,299 | 6/1898 | Perrottet | 450/144 |
| 929,169 | 7/1909 | Wood . | |
| 1,367,420 | 2/1921 | Munter | 2/44 X |
| 3,554,190 | 1/1971 | Kaplan | 2/44 X |
| 4,175,553 | 11/1979 | Rosenberg | 2/44 X |
| 4,572,167 | 2/1986 | Brunswick | 2/44 X |
| 4,627,109 | 12/1986 | Carabelli et al. | 2/44 |

Primary Examiner—Henry S. Jaudon
Attorney, Agent, or Firm—Burd, Bartz & Gutenkauf

[57] ABSTRACT

A back brace to provide firm support to the lumbar sacro area of the back, includes an elastic inner wrap that circumferentially stretches around the torso and fastens in the front. The inner wrap carries a back support panel. An elastic outer wrap overlaps the inner wrap with the back support panel between it and the inner wrap. A support pad is carried outside the outer wrap. The support panel carries resilient flexure means that fit in the small of the back when the inner and outer wrap are wrapped around the torso and secured in front. The support pad disburses the supportive force of the support panel about the lumbar sacro area of the back.

19 Claims, 3 Drawing Sheets

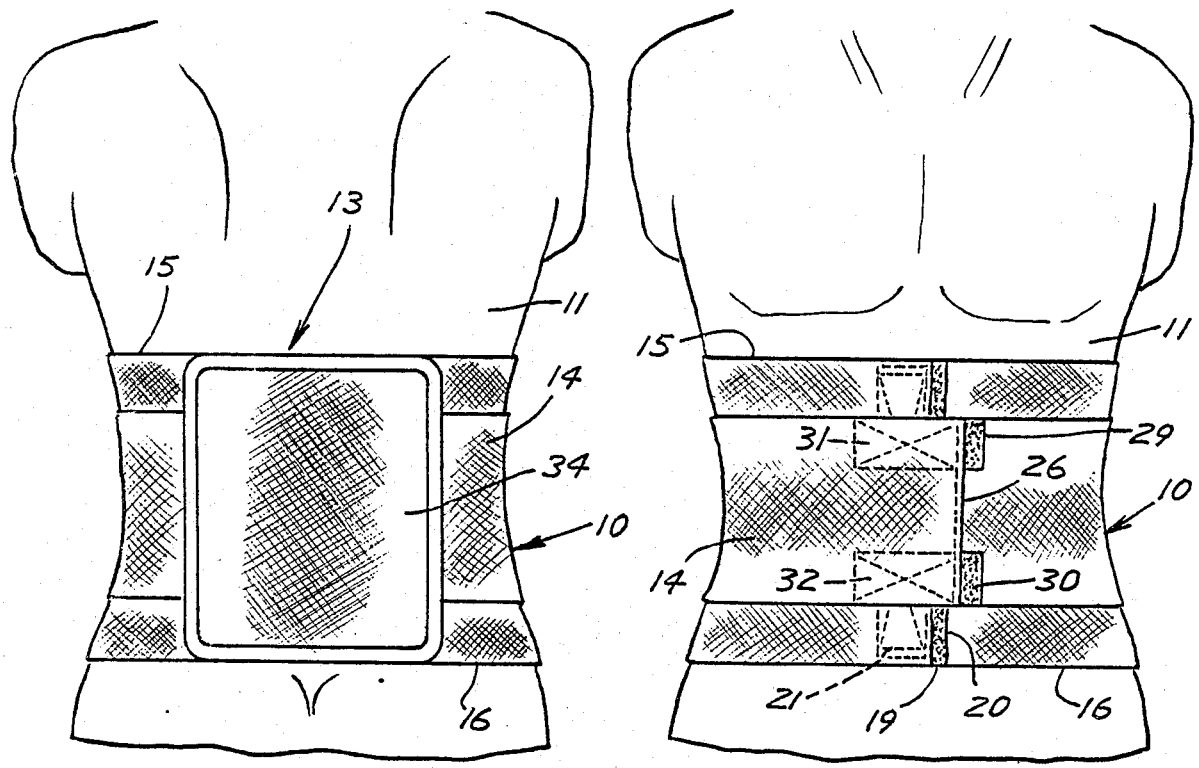
FIG. 1
FIG. 2
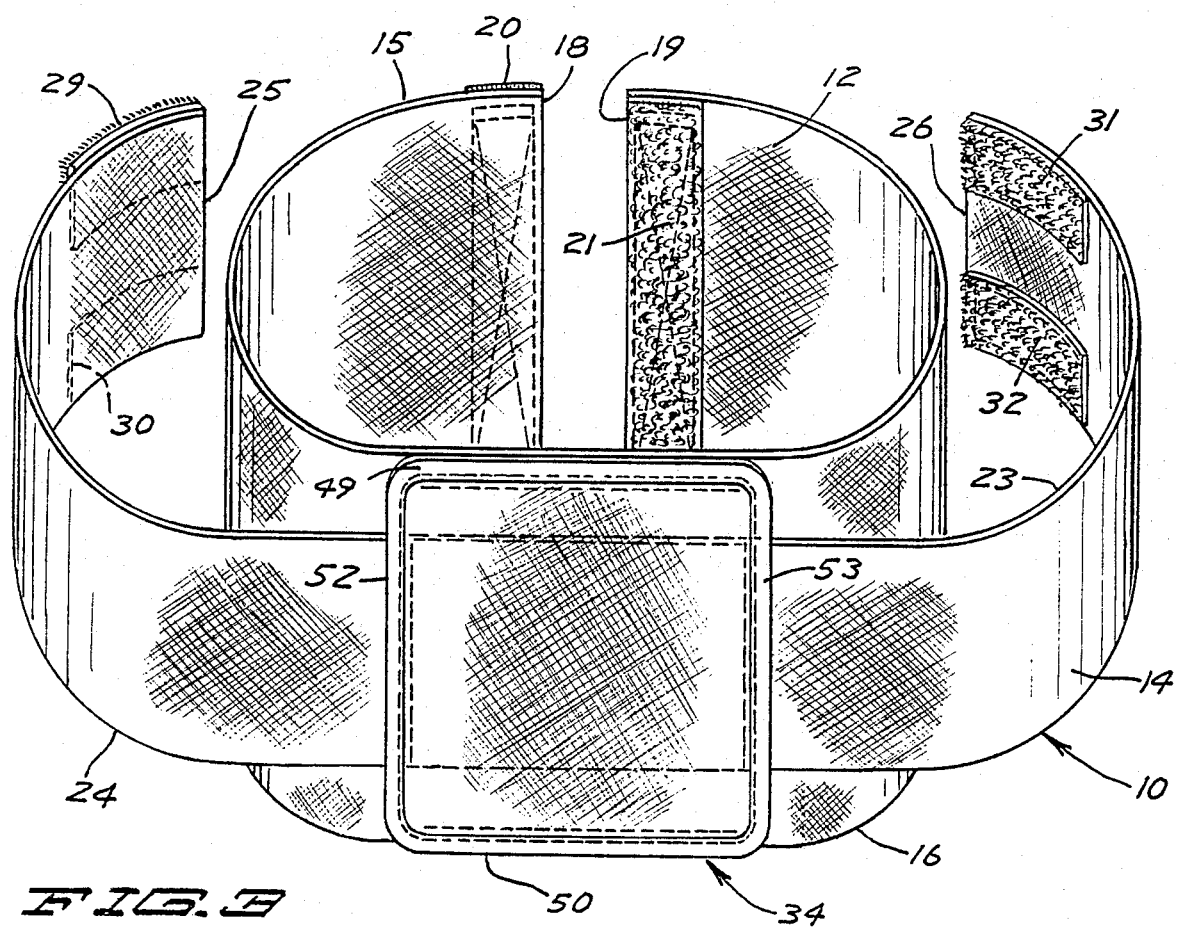
FIG. 3

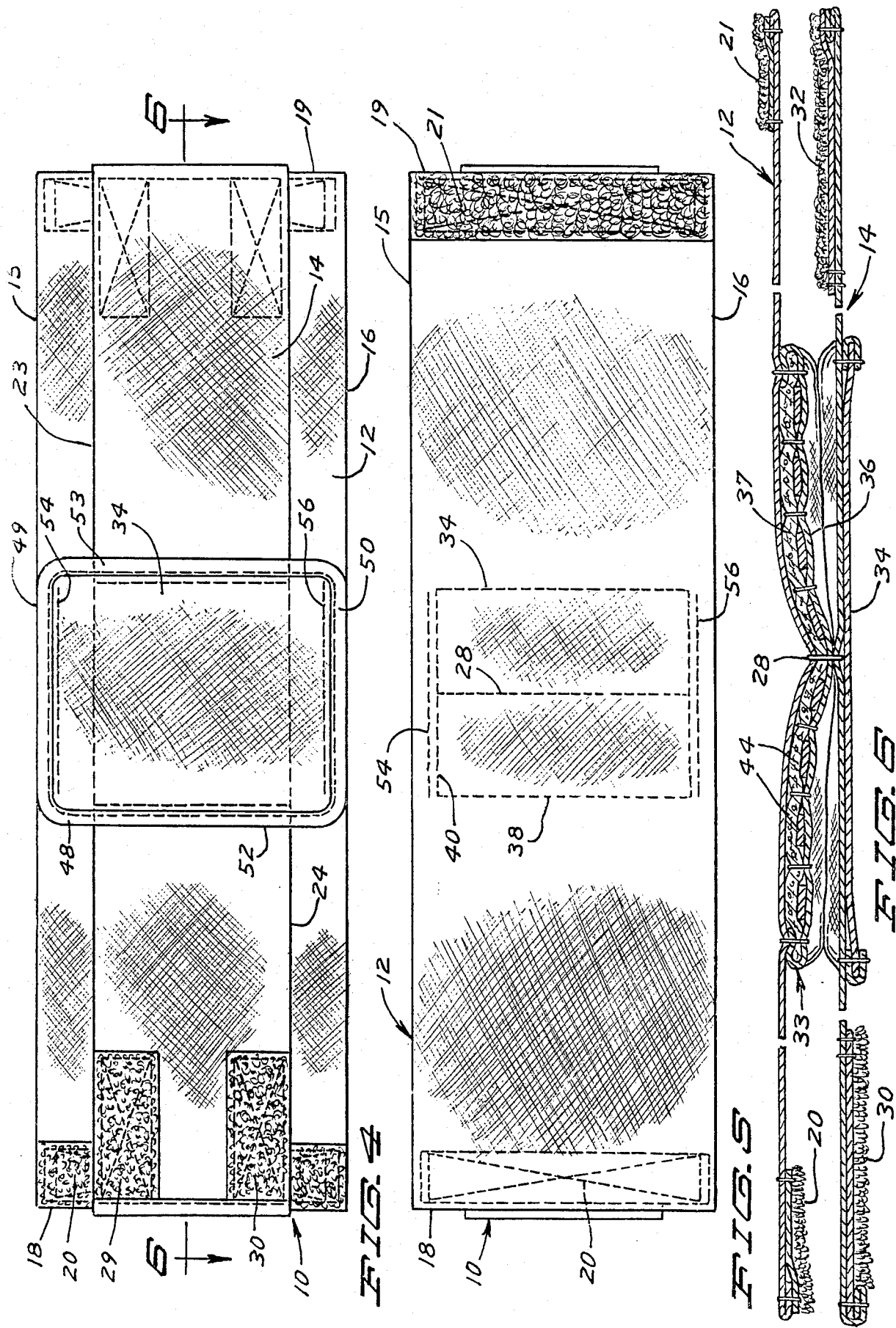

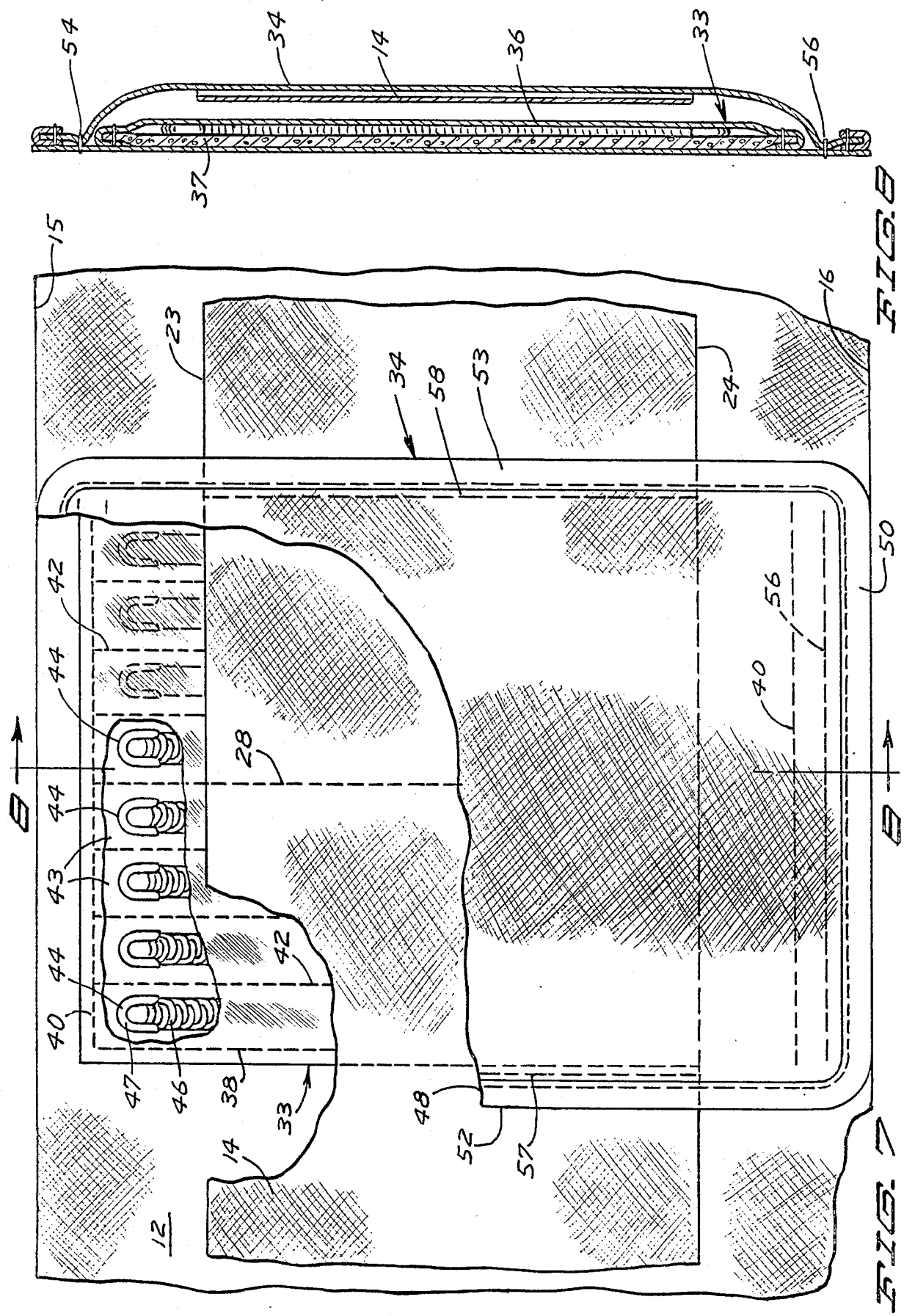

BACK BRACE

BACKGROUND OF THE INVENTION

The largest muscle grouping of the human body occurs in the area of the small of the back or the lumbar region. Muscles from this group are used for practically all activities such as walking, running, standing, sitting, squatting, lifting, throwing, bending and straightening up again. Injury of a muscle in this group is usually detrimental to normal movement and requires support therapy. When engaging in certain activities, many individuals with a propensity toward injury should protect this region of the back even without pre-existent injury. Various devices are available. Some devices completely immobilize the back which can lead to muscle atrophy, discomfort and very limited mobility. Installation and removal of such devices can be difficult and time consuming. However, use of such devices is far preferable to use of none and saves the back from pain and further injury. Sometimes a simple back wrap is used. This involves an elastic wrap wound once or twice around the back and then fastened. The wrap is typically relatively wide, and tends to bunch toward one point. Smaller width wraps can be used, but they too tend to bunch in one point and also tend to migrate during use. They provide equal support to the entire area around the torso and do not provide for localized support in the lumbar region.

Back support is important not only in the case of repair of muscle tissue, but also ligaments and bones. Injury to the sacroiliac region is common upon a fall and can take a great deal of time to repair. Certain arthritic conditions may make local immobilization of the bones in the sacro area desirable without entire immobilization being indicated or necessary.

–SUMMARY OF THE INVENTION

The invention relates to a back brace to provide a good deal of support to the lumbar and sacro regions of the back without complete immobilization of the area. The brace is usable for situations involving low back sprain, minor disc conditions and similar injuries or adverse back conditions. The brace includes an inner wrap wound once around the waist. Forward edges come together for fastening at the front. The inner wrap encompasses the human torso from approximately the lower rib cage origin on the upper extremity, to the abdominal region just superior to the buttocks at the lower extremity, it being understood that there will be substantial variation from one individual to another. A flexible resilient back support panel is fixed to the inner wrap on the outer surface in spanning relationship to the lumbar area of the back. The support panel carries resilient means such as spring stays for bearing against the lumbar and sacro back regions for lending support thereto. A support pad is fastened to the inner wrap at its upper and lower edges in covering relationship to the support panel. The support panel keeps the edges of the wrap spread apart from top to bottom for disbursing the support over the lumbar sacro area. An outer wrap is fixed to the lateral edges of the support pad and wraps around the body in overlapping relationship to the inner wrap. The outer wrap is somewhat narrower than the inner wrap and is fixed only to the lateral edges of the support pad so as to circumferential disburse the pressure of the support pad. The support pad presses against the support panel to hold it in proper position. Together the inner and outer wraps hold the flexible support panel and support pad in position over the lumbar sacro region of the back to provide substantial support yet permit limited movement.

IN THE DRAWINGS

FIG. 1 is a rear elevational view of the back brace of the invention installed upon a human torso;

FIG. 2 is a front elevational view of the back brace of FIG. 1;

FIG. 3 is a perspective view of the back brace of FIGS. 1 and 2 in an open configuration;

FIG. 4 is a distal or outside view of the back brace of FIGS. 1 and 2 in a flat configuration;

FIG. 5 is a proximal or inside view of the back brace of FIG. 4;

FIG. 6 is an enlarged sectional view of a portion of the back brace of FIG. 4 taken along the line 6—6 thereof;

FIG. 7 is an enlarged view of the central portion of the back brace shown in FIG. 4 partially fragmented for purposes of illustration; and FIG. 8 is a sectional view of a portion of the back brace shown in FIG. 7 taken along the line 8—8 thereof.

DESCRIPTION OF A PREFERRED EMBODIMENT

Referring to the drawings, there is shown in FIGS. 1 and 2 a back brace indicated generally at 10 installed on a human male torso 11, the back view being shown in FIG. 1 and the front view in FIG. 2. Brace 10 encompasses the torso from the region of the mid to lower rib cage at the upper extremity and approximately the lower abdominal area just superior to the buttocks at the lower extremity in spanning relationship to the waist. The upper and lower extremities of the torso encompassed by the brace will vary significantly from one individual to another due to individual variations in stature and body proportions. Brace 10 encompasses the small of the back or lumbar sacro region 13 and is effective to compress the lumbar area of the back and disperse a supportive force about it in order to alleviate muscle tension as may occur during significant body stress while lifting, engaging in active sports or the like. Brace 10 is effective for facilitating repair of damaged back muscles or ligaments and alleviating pain caused by certain arthritic conditions. Brace 10 is also effective to promote healing and repair of certain mild to moderate intervertebrae disc conditions, for post surgical recovery from disc or any other lumbar spine procedures and the like. Brace 10 does not totally immobilize the back in splint-type fashion, however does provide a great deal of localized support to the small of the back or lumbar area without a total inhibition from movement.

As shown in FIGS. 1 through 5, brace 10 includes an inner wrap 12 and an outer wrap 14 overlaps the inner wrap 12. Inner wrap 12 is comprised as a sheet-like member of linearly elastic material or an elongate longitudinally elastic band having an upper edge 15 and a lower edge 16 comprising upper and lower extremities of the brace 10 when installed on a torso. Wrap 12 has a width defined by the distance between the upper and lower edges 15, 16 encompassing the torso from roughly the area of the lower to middle rib cage at the top to the lower abdominal or upper hip region at the bottom. The length of the inner wrap 12 is slightly less than the smallest circumferential dimension of the waist so that it will be required to be in tension when stretched about the torso 11. Inner wrap 12 has forward edges 18 and 19 which come together at the front of the torso 11 when the wrap is stretched around the waist in tension. Fastening means releasably fasten the edges together. First forward edge 18 has a vertical fastening strip 20 that is outwardly facing. Opposite forward edge 19 has an inwardly facing vertical fastening strip 21 to overlap the outwardly facing fastening strip 20 when the edges are brought together at the front of the torso. The fastening strips 20, 21 can be formed of synthetic material of the type that adheres when pressed together such as commonly sold under the trademark Velcro.

Outer wrap 14 comprises a second elongate band of sheet-like material that is longitudinally elastic or circumferentially stretchable when installed about the human torso. The outer wrap 14 is narrower than the inner wrap 12, having top and bottom edges 23, 24 between the respective top and bottom edges 15, 16 of inner wrap 12. The outer wrap has forward edges 25, 26 that come together at the front of the torso when the wrap is stretched about the waist overlapping the inner wrap 12. The outer wrap 14 is connected to the inner wrap 12 by a single longitudinal seam of vertical stitching 28 shown in FIG. 5 and to be described more fully. First forward edge 25 of the outer wrap 14 carries upper and lower horizontal fastening strips 29, 30 generally aligned with the upper and lower edges 23, 24 respectively and extending rearwardly from the forward edge. Fastening strips 29, 30 are outwardly facing when the outer wrap in installed about the inner wrap 12. Second forward edge 26 carries inwardly facing, generally horizontal fastening strip 31, 32 generally aligned with the upper and lower edges 23, 24 and extending rearwardly from the front edge 26. When the outer wrap is installed about the human torso, the second edge 26 is overlapped the first edge 25 such that the fastening strips 29, 30 on the first edge meet the fastening strips 31, 32 on the second edge and adhere. The fastening strips again are formed of synthetic material that adheres when pressed together such as Velcro. The length of the strips rearwardly of the forward edges lends adjustability to the outer wrap 14 or a measure of adjustability to the tension placed in the outer wrap 14 as it is wrapped around the inner wrap 12.

A back support assembly is fixed to the rear of the back brace 10 in covering relationship to the lumbar sacro region 13 of the back. A back support panel 33 is located between the inner wrap 12 and the outer wrap 14. The support panel 33 is covered by a support pad 34 which is secured to back brace 10 substantially covering the support panel 33. It is fixed exteriorly to the outer wrap 14, fastened at upper and lower edges to the inner wrap 12 and at lateral edges to the outer wrap 14. Support pad 34 works on support panel 33 to spread the supportive force about the lumbar sacro region of the back.

Referring to FIGS. 7 and 8, back support panel 33 has a height coextensive with the width of the inner wrap 12 and covers the small of the back or the lumbar sacro region 13. Support panel 33 is relatively stiff and resilient and pulls into the lumbar sacro region of the back upon tensioning of the inner wrap 12 about the torso, to conform to the anatomical structure of the back. Support panel 33 has a cover compising an outer layer 36 and an inner layer 37 (FIG. 8) that are connected together and to the outer surface of inner wrap 12 by vertical and horizontal peripheral stitching 38, 40. The outer layer 36 is formed of an inelastic relatively strong material such as vinyl. Inner layer 37 is preferably formed of a soft material such as foam rubber for purposes of comfort. The inner and outer layers 36, 37 closed by stitching 38, 40 form an envelope or closure for resilient stay means provided therein to support the lumbar sacro area of the back when the panel is properly positioned. A plurality of parallel spaced apart vertical seams 42 are formed between the outer and inner layers 36, 37. Seams 42 form a plurality of elongate upright, parallel pockets 43 between the outer and inner layers 36, 37. The pockets 43 extend from proximate the upper edge of inner wrap 12 to a location proximate but just short of the lower edge of the inner wrap 12. Each of the pockets 43 carries an elongate longitudinal resilient stay member 44. Each stay member 44 is longitudinally inflexible but resilient about axes perpendicular to the longitudinal axis thereof. Various types of members could provide suitable stay members with the required resiliency and spring constant. As shown, each stay member is comprised of an elongate body portion 46 comprised of a pair of interleaved helical springs that are flattened together, terminated with an end cap 47. Stay 44 so comprised provide a measure of resiliency about axes perpendicular to the plane of the drawings of FIG. 7 and FIG. 8 so as to impart a measure of resiliency to the back support panel 33. The rectangular configuration of back support panel 33 covers the mid portion of the inner wrap 12 and the lumbar sacro area 13 of the back when inner wrap 12 is tensioned about the torso of the body.

The single vertical seam 28 fixing outer wraps 14 to inner wraps 12 is coincidental with one of the seams 42 forming one of the pockets 43.

Support pad 34 is comprised of a piece of flexible sheet-like material that is relatively inelastic such as canvas. Support pad 34 works to disperse the supportive force provided by the support panel 33 across the lumbar sacro region. Support pad 34 has edges with a continuous binding 48 and including upper and lower edges 49, 50 substantially coincident with the upper and lower edges 15, 16 of the inner wrap 12. Support pad 34 has first and second lateral edges 52, 53 at the lateral sides thereof in covering relationship to the lateral edges of the support panel 34. A top stitching or horizontal seam 54 fixes the upper edge 49 of the support pad 34 proximate the upper edge 15 of the inner wrap 12. A lower horizontal seam or stiching 56 fixes the lower edge 50 of the support pad 34 adjacent the lower edge 16 of the inner wrap 12. Support pad 34 is fixed to the inner wrap 12 solely by means of the horizontal seams 54, 56 at the peripheral upper and lower edges 49, 50. Tensioning of inner wrap 12 pulls the upper and lower edges of support pad 34.

The support pad 34 covers a rear portion of outer wrap 14. First lateral edge 52 of the support pad 34 is fixed to the outer surface of the outer wrap 14 by a vertical seam or stitch 57. The second lateral edge 53 of the support pad 34 is fixed to the outer wrap 14 by means of a second vertical stitch or seam 58. The vertical seams 57, 58 extend only so much along the lateral edges 52, 53 of the support pad 34 as is overlapped with respect to the outer wrap 14. The sole means by which the support 34 is fixed to the outer wrap 14 is the vertical seams 57, 58. Tensioning of the outer wrap 14 when wrapping it around a torso imposes a circumferential pull upon the lateral edges 52, 53 of support pad 34.

In use, inner wrap 12 is extended about the waist in tension with the front edges approaching one another at the front of the body and the back support panel poised over the small of the back. Front edges 18, 19 are connected by overlapping them and pressing them together. Tensioning of the inner wrap 12 pulls the back support panel into the small of the back and stretches the horizontal top and bottom edges 49, 50 of the support pad. The elasticity of the inner wrap 12 alone lends a certain measure of support to the lumbar sacro area of the back and tends to compress muscles in a rested state. Next the outer wrap 14 is brought around the torso 11 in tension and the front edges are secured. The length of the fastening members 29, 30, 31, 32 permits adjustment of the amount of tension provided by the outer wrap. The wrap reinforces the supportive effect of the inner wrap. It also pulls the intermediate portions of the lateral edges of the support pad 34 into the small of the back which results in pushing support panel 33 into the small of the back. This results in an anatomically correct fit of the support panel in the small of the back producing an optimal effect in lending support to the lumbar sacro area of the back. The support pad, fixed at upper and lower edges to the inner wrap, and at latter edges to the outer wrap, not only disburses the supportive force of the support panel, but prevents bunching and migration of the wraps.

Brace 10 is light and flexible. It provides a good deal of firm support for the back and precompresses certain muscles of the back such that upon exertion the muscles begin to stretch toward normal position and then beyond so as to prevent hyperextension and strains.

While there is shown and described a preferred embodiment of a back brace according to the invention, it will be apparent that certain changes and deviations can be had with out departing from the scope and spirit of the claims.

The embodiment of the invention in which an exclusive property or priveledge is claimed are defined as follows:

1. A back brace to encompass the waist of an individual in spanning relationship of the torso approximately between the lower rib cage at the upper extremity and the upper hip region at the lower extremity, comprising:
   an inner wrap comprised as a first elongate circumferentially elastic band having top and bottom edges for wrapping in tension around the human torso in spanning relationship to the waist, and having first and second forward edges that come together about the front of the torso, and releasable fastening means on the first and second forward edges to fasten them together with the first band wrapped in tension around the torso;
   a back support panel fixed to the inner wrap centrally thereof positioned to be in covering relationship to the small of the back when the inner wrap is wrapped around a torso with the first and second forward edges brought together about the front of the torso, said back support panel including cover means and resilient flexure means located in the cover means substantially coextensive therewith of sufficient size to span the small of the back and be brought into bearing relationship with the small of the back upon tensioning of the inner wrap about the torso;
   an outer wrap comprised as a second elongate circumferentially elastic band having top and bottom edges for wrapping around the torso in overlapping relationship to the inner wrap, and forward edges that come together about the front of the torso, releasable fastening means on the forward edges of the outer wrap for fastening them together, a back support pad for pressing against the back support panel to bring it into bearing relationship to the small of the back, said support pad positioned in covering relationship to the back support panel, said support pad having a first pair of edges comprised as upper and lower edges, and a second pair of edges comprised as parallel lateral side edges;
   means fixing said inner wrap to one of said pairs of edges of the support pad;
   means fixing said outer wrap to the other pair of edges of the support pad.

2. The back brace of claim 1 wherein: said means on the first and second forward edges for fastening them together include an outwardly facing fastening strip on one of the edges, and an inwardly facing fastening strip on the other edge for overlapping the outwardly facing fastening strip, said fastening strips including synthetic material of the type that adheres when pressed together.

3. The back brace of claim 1 wherein: said outer wrap is fixed to the lateral edges of the support pad, and said inner wrap is fixed to the top and bottom edges of the support pad.

4. The back brace of claim 3 wherein: said inner wrap has a width dimension between the upper and lower edges that is greater than the width dimension of the outer wrap.

5. The back brace of claim 4 wherein: fastening means on the forward edges of the outer wrap include at least one elongate outwardly facing fastening strip extended from the first forward edge of the outer wrap rearwardly, at least one elongate inwardly facing fastening strip extended rearwardly from the second forward edge for overlapping with the fastening strip on the first forward edge upon tensioning of the outer wrap around the waist, said fastening strips being comprised of synthetic material of the type that adheres when pressed together.

6. The back brace of claim 3 wherein: means fixing the upper and lower edges of the support pad proximate the upper and lower edges of the inner wrap are comprised as sewn seams; and means fixing the first and second lateral edges of the support pad to the outer wrap are comprised as sewn seams.

7. The back brace of claim 1 wherein: said support pad has a width according to the inner wrap, sewn means fixing the upper and lower edges of the support pad proximate the upper and lower edges of the inner wrap, sewn means fixing the parallel lateral edges of the support pad to the outer wrap.

8. The back brace of claim 1 wherein: said cover means for the back support panel includes an inner cover and an outer cover fixed to the inner cover forming a closed envelope, a plurality of parallel spaced apart seams formed between the outer and inner covers forming a plurality of parallel pockets, resilient stay means including a plurality of resilient elongate stay members located in the pockets.

9. The back brace of claim 8 wherein: each said stay member is comprised of a pair of helical springs interleaved and flattened.

10. The back brace of claim 8 wherein: said support pad has a width according to the width of the inner wrap, means fixing the upper and lower edges of the support pad proximate the upper and lower edges of the inner wrap, means fixing the parallel lateral edges of the support pad to the outer wrap.

11. The back brace of claim 10 wherein: means fixing the upper and lower edges of the support pad proximate the upper and lower edges of the inner wrap are comprised as sewn seams; and means fixing the first and second lateral edges of the support pad to the outer wrap are comprised as sewn seams.

12. The back brace of claim 11 wherein: said inner wrap has a width between the top edge and bottom edge sufficient generally to span the area of the torso between approximately the lower rib cage at the top extremity and the upper hip region at the bottom extremity.

13. A back brace to encompass the waist of an individual and provide localized support to the lumbar region of the back, comprising:

an inner wrap comprised as a first elongate circumferentially elastic band having top and bottom edges for wrapping in tension around the human torso in spanning relationship to the waist and of a width to span the torso from an area of approximately the lower rib cage at the upper extremity and the upper hip region at the lower extremity, said inner wrap having first and second forward edges that come together about the front of the torso, and fastening means on the first and second forward edges to releasably fasten them together;

a back support panel fixed to the outer surface of the inner wrap centrally thereof positioned to be in covering relationship to the small of the back when the inner wrap is wrapped around the torso in tension, said back support panel including a generally rectangular cover having upper and lower edges located adjacent upper and lower edge portions of the inner wrap, said cover having a plurality of parallel generally vertical pockets, a plurality of resilient flexible stay members located in the pockets of the cover and brought into bearing relationship with the lumbar area of the back upon tensioning of the first wrap about the torso;

an outer wrap comprised of a second elongate circumferentially elastic band having top and bottom edges for wrapping in tension around the torso in overlapping relationship to the inner wrap, said outer wrap having a width less than the width of the inner wrap and being centrally fixed to the inner wrap having first and second forward edges that come together about the front of the torso, and fastening means on the forward edges of the outer wrap to releasably fasten them together;

a support pad disposed in covering relationship to the back support panel to spread the supportive forces of the back support panel about the lumbar sacro region of the back, said support pad being generally rectangular and having upper and lower edges, means fixing the upper and lower edges of the support pad to upper and lower edge portions of the inner wrap, and said support pad having first and second side edges, means fixing the first and second side edges to portions of the outer wrap whereby said support pad bears against the back support panel upon tensioning of the inner and outer wraps about the torso.

14. The back brace of claim 13 wherein: said means on the forward edges of the inner wrap include an outwardly facing fastening strip on one of the edges, and an inwardly facing fastening strip on the other edge for overlapping the outwardly facing fastening strip, said fastening strips including synthetic material of the type that adheres when pressed together.

15. The back brace of claim 14 wherein: fastening means on the forward edges of the outer wrap include an elongate outwardly facing fastening strip extended from the first forward edge of the outer wrap rearwardly, an elongate inwardly facing fastening strip extended rearwardly from the second forward edge for overlapping with the fastening strip on the first forward edge upon tensioning of the outer wrap around the waist, said fastening strips being comprised of synthetic material of the type that adheres when pressed together.

16. The back brace of claim 15 wherein: means fixing the upper and lower edges of the support pad proximate the upper and lower edges of the inner wrap are comprised as sewn seams; and means fixing the first and second lateral edges of the support pad to the outer wrap are comprised as sewn seams.

17. The back brace of claim 15 wherein: said stay members are comprised as flattened interleaved helical springs.

18. A back brace to encompass the waist of an individual in spanning relationship of the torso approximately between the lower rib cage at the upper extremity and the upper hip region at the lower extremity, comprising:

an inner wrap comprised as a first elongate circumferentially elastic band having top and bottom edges for wrapping in tension around the human torso in spanning relationship to the waist and of a width to span the torso from an area approximately the lower rib cage at an upper extremity and the upper hip region at a lower extremity, said first elastic band having first and second forward edges that come together at the front of the torso, and fastening means on the forward edges to fasten them together with the first band wrapped in tension around the torso;

an outer wrap comprised of a second elongate circumferentially elastic band having top and bottom edges for wrapping in tension about the torso in overlapping relationship to the inner wrap, said outer wrap having a width less than the width of the inner wrap and being centrally fixed to the inner wrap, said outer wrap having first and second forward edges that come together in front of the torso when the outer wrap is wrapped in tension around the torso, and a fastening means on the forward edges to fasten them together when the inner wrap is wrapped tension around the torso; and back support means including flexible resilient stays secured between the inner and outer wraps in position overlying the small of the back so as to be brought into bearing engagement with the small of the back, upon wrapping the inner and outer wraps around the torso and fastening the forward edges at the front of the torso, and support pad means fixed exteriorly to the resilient stays and fixed to portions of the inner wrap and outer wrap to press the flexible stays into the small of the back when the inner and outer wraps are fastened around the torso.

19. The back brace of claim 18 including: cover means covering resilient stiffening members, said cover means having a plurality of elongate pockets, one of said stiffening members being located on each pocket.

* * * * *